United States Patent [19]
Hatta et al.

[11] Patent Number: 6,071,008
[45] Date of Patent: Jun. 6, 2000

[54] METHOD OF MEASURING HEAT CAPACITY OF SAMPLE

[75] Inventors: Ichiro Hatta, Nagoya; Haruhiko Yao, Yokohama; Kenji Ema, Fujisawa, all of Japan

[73] Assignee: Nagoya University, Aichi, Japan

[21] Appl. No.: 09/014,569

[22] Filed: Jan. 28, 1998

[30] Foreign Application Priority Data

Jan. 28, 1997 [JP] Japan .................................. 9-013771

[51] Int. Cl.[7] ............................................... G01J 5/02
[52] U.S. Cl. ........................... 374/31; 374/131; 374/133
[58] Field of Search .................... 374/5, 11, 31, 374/33

[56] References Cited

U.S. PATENT DOCUMENTS

| | | | |
|---|---|---|---|
| 2,800,793 | 7/1957 | Oliver | 374/33 |
| 4,178,800 | 12/1979 | Thomann | 374/33 |
| 4,963,499 | 10/1990 | Stockton et al. | 374/31 |
| 5,335,993 | 8/1994 | Marcus et al. | 374/33 |
| 5,439,291 | 8/1995 | Reading | 374/33 |
| 5,549,387 | 8/1996 | Schawe et al. | 374/11 |
| 5,599,104 | 2/1997 | Hakamura et al. | 374/11 |
| 5,713,665 | 2/1998 | Kato et al. | 374/31 |

FOREIGN PATENT DOCUMENTS

| | | |
|---|---|---|
| 59-135356 | 8/1984 | Japan . |
| 05-014200 | 4/1993 | Japan . |
| 07-103921 | 4/1995 | Japan . |

OTHER PUBLICATIONS

P. Sullivan and G. Seidel, "Steady State, ac–Temperature Calorimetry", Physical Review, vol. 173, No. 3, 1968, pp. 679–685.

G.S. Dixon, S. G. Black, C. T. Butler and J.K. Jain, "A Differential AC Calorimeter for Biophysical Studies", Analytical Biochemistry, vol. 121, Jul. 1982, pp. 55–61.

H. Yano and I. Hatta, "An ac Calorimetric Method for Liquid", Japanese Journal of Applied Physics, vol. 27, No. 1, 1988, pp. L121–L122.

J.E. Graebner, "Modulated–bath calorimetry", Review of Scientific Instruments, vol. 60, No. 6, Jun. 1989, pp. 1123–1128.

Tamio Oshima, Thermal Diffusivity Measurement of Thin Films by AC–Method Using Phase Shift, The Fourteenth Japan Symposium of Thermophysical Properties (1993), pp. 83–86.

Ryozo Kato, Thermal Diffusivity Measurement of Films by Laser Irradiation AC Calorimetric Method, The Sixteenth Japan Symposium on Thermophysical Properties (1995), pp. 93–96, with English abstract.

Kenji Ema, Some Aspects in Recent Development in ac–Calorimetry, Netsu Sokutel 20(3)(1993) pp. 146–153.

*Primary Examiner*—G. Bradley Bennett
*Assistant Examiner*—Gail Verbitsky
*Attorney, Agent, or Firm*—Sughrue, Mion, Zinn, Macpeak & Seas, PLLC

[57] ABSTRACT

A tube 12 made of stainless steel is arranged in a thermal bath 13 and an AC current is supplied to the tube to apply an AC heat directly to the tube and a liquid sample contained therein. An AC temperature of the tube 12 is detected by a thermocouple 19. An amplitude of the AC heat, and a phase difference between the AC heat and the AC temperature are detected. The above measurement is performed for the vacant tube, the standard liquid sample containing tube and the liquid sample containing tube to derive amplitudes $\Delta T_c$, $\Delta T_r$ and $\Delta T_s$ and phase differences $\phi_c$, $\phi_r$ and $\phi_s$. Then, a heat capacity $\rho_s \cdot C_s$ per a unit volume of the liquid sample is calculated from a following equation $$\rho_s \cdot C_s = [\{\sin(\phi_s)/\Delta T_s - \sin(\phi_c)/\Delta T_c\}/\{\sin(\phi_r)/\Delta T_r - \sin(\phi_c)/\Delta T_c\}]\rho_r$$

wherein $C_r$ and $\rho_r$ denote heat capacity and density of the standard liquid sample, respectively. In this manner, the heat capacity of the liquid sample can be measured precisely without being affected by heat leakage.

16 Claims, 5 Drawing Sheets

FIG_1
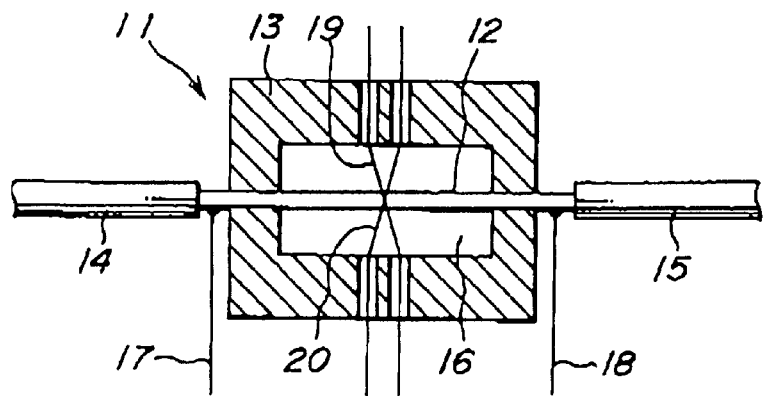
FIG_2A
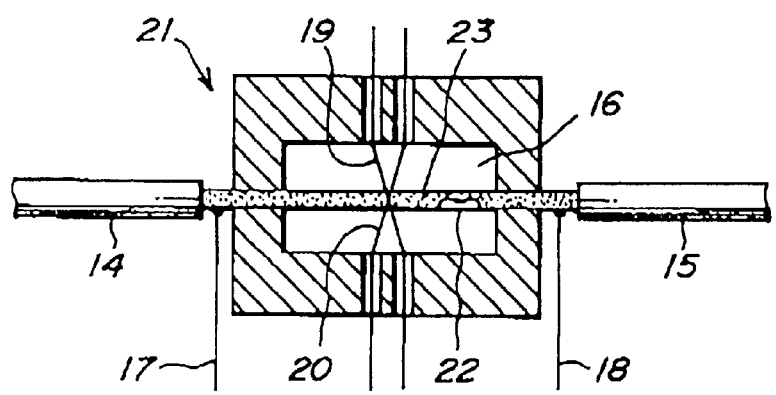
FIG_2B
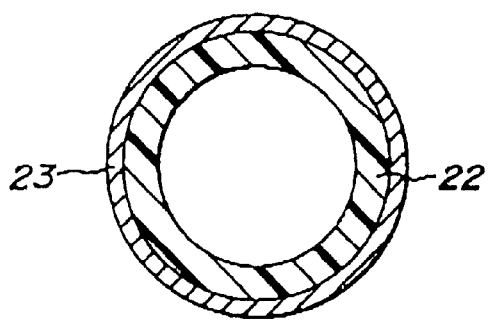

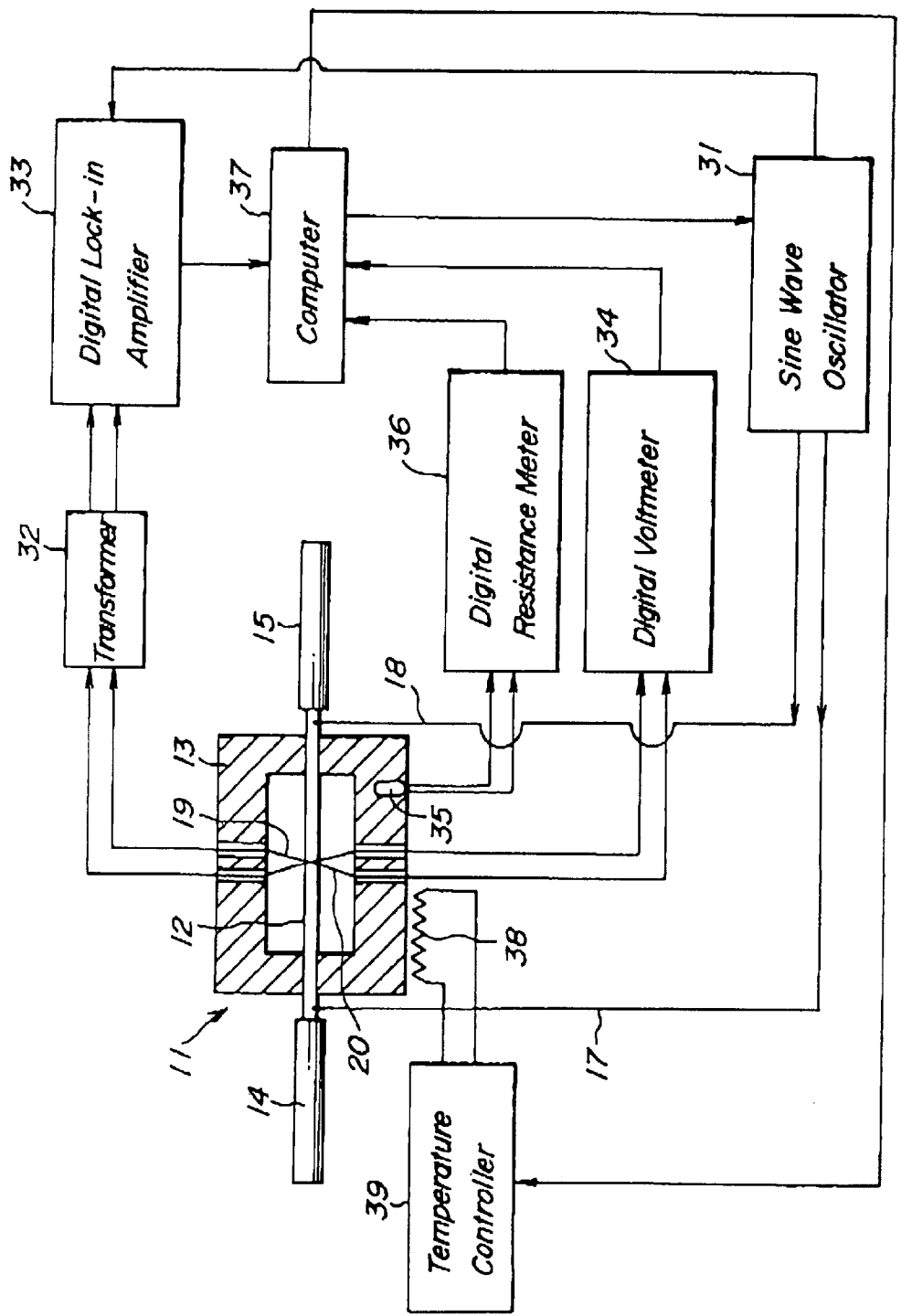

FIG_5
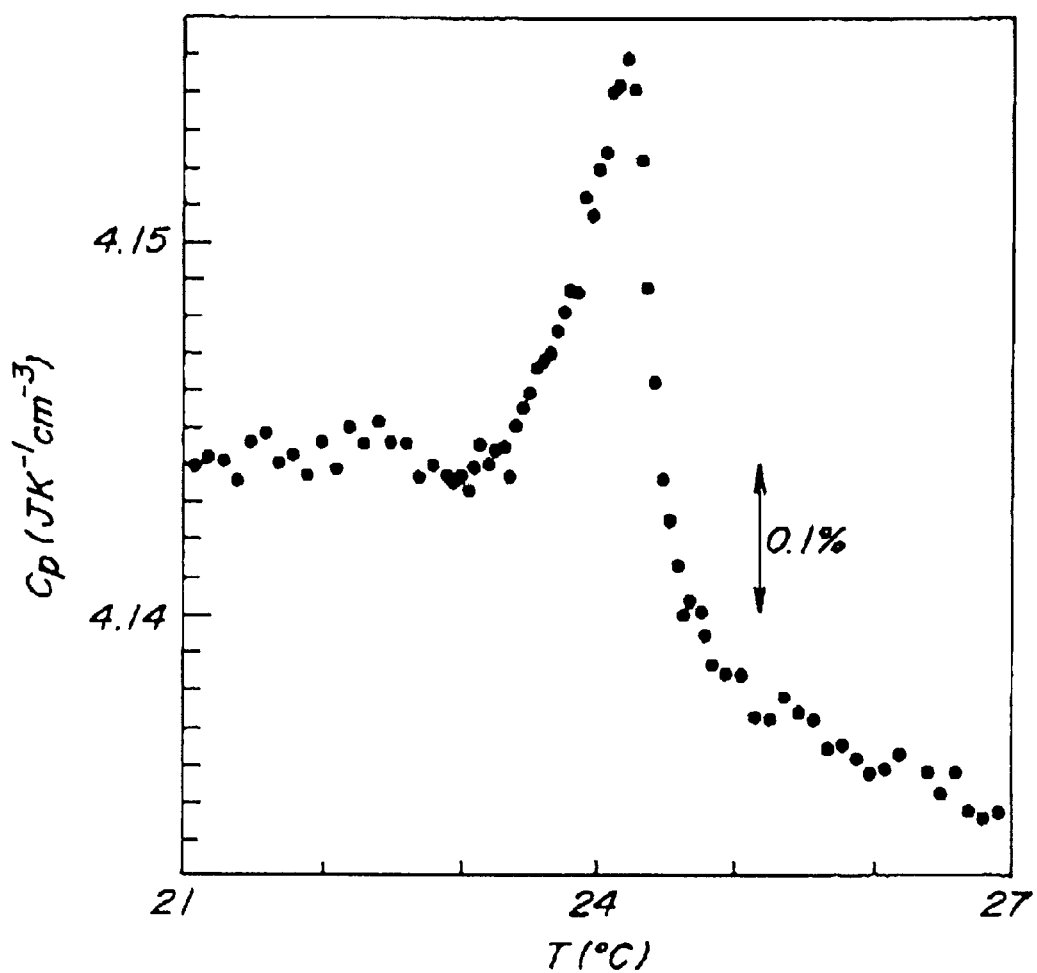

METHOD OF MEASURING HEAT CAPACITY OF SAMPLE

BACKGROUND OF THE INVENTION

1. Field of the Invention

This invention relates to a method of measuring heat capacity of a sample, and more particularly to a method of measuring an absolute value of heat capacity of a sample by AC calorimetry with high accuracy.

2. Related Art Statement

AC calorimetry has been well known as a method of measuring heat capacity of a liquid sample, in which the liquid sample is periodically heated in an alternate manner and the heat capacity is measured by detecting a temperature modulation of the liquid sample. In the past, heat capacity of a liquid sample was measured by filling a sample cell formed by two opposing plates with the liquid sample. However, in this method, it is very difficult to keep a distance between the two plates constant, and thus measuring accuracy is limited. Moreover, alternate temperature of the vacant cell cannot be precisely measured because two plates are not thermally contacted with each other when the sample cell is not filled with the liquid sample. In this manner, heat capacity of the sample cell itself cannot be measured accurately, and this results in that an absolute value of heat capacity of the liquid sample cannot be measured.

To remove these defects, the inventors of the present application have developed an improved light irradiation type AC calorimetry, which has been described in "Heat and Temperature Measurement and Thermal Analysis", Heat Measurement Research, pp. 74–81, 1973, "Japanese Journal of Applied Physics", Vol. 20, No. 11, pp. 1995–2011, November 1981, and Utility Model Publication of Application 5-14200.

In the heat capacity measurement by the known light irradiation type AC calorimetry of the above mentioned Utility Model Application Publication 5-14200, a sample cell is formed by arranging a very small tube having a very thin wall and a very small diameter in a thermal bath such that its both ends are supported by the thermal bath. A liquid sample contained in the tube is heated in an alternating manner, for example, at 0.2–10 Hz repetition frequency by irradiating light intermittently to this tube by means of a chopper from outside of the thermal bath, and a temperature modulation (called AC temperature) of the liquid sample is then detected by the thermo-sensor provided on surface of the tube. Then, an amplitude of the thus detected AC temperature is measured. Prior to or after the above measurement, amplitudes of AC temperatures are detected for the vacant tube in the sample cell as well as for the tube filled with a standard liquid having known heat capacity and density. Thus, the heat capacity of the liquid sample is measured or derived from the amplitudes of these three AC temperatures. This light irradiation type AC calorimetry is based on a fact that an AC component of the temperature change in the liquid sample, i.e. the amplitude of AC temperature, is in inverse proportion to the heat capacity of the liquid sample when the liquid sample is heated periodically.

In the above mentioned light irradiation type AC calorimetry, it is advantageous that the absolute value of the heat capacity of a liquid sample can be measured much more precisely. But recently, it has been required to develop a method which can measure a slight change in heat capacity of a solution having a very small amount of substance dissolved therein. However it has been confirmed that such a requirement could not be satisfied with the light irradiation AC calorimetry. The reason is the following.

It is confirmed that a measurement error caused by heat leakage is substantially large in the known light irradiation type AC calorimetry. In the AC calorimetry, it is necessary to consider the heat leakage. However, in practice, it is very difficult to perform the AC calorimetry while the heat leakage is corrected. Therefore, in the known AC calorimetry, a condition of $1/\tau_e < \omega$ is satisfied so that a correction term of $1/\omega^2 \tau_e^2$ can be neglected. Herein $\omega$ is an angular frequency of AC heat flow, and $\tau_e$ is an external relaxation time, which is a physical amount defined by a product between heat capacity of a sample and thermal resistance between the sample and thermal bath. Accordingly, the need for compensating the heat leakage is avoided by making a speed of the heat leakage from the tube to the thermal bath less than the AC heat period. Thus, the heat capacity has to be measured by setting a lower limit for the repetition frequency of light irradiation. However, it is required to make the sample cell tube as small as possible, because the liquid heat diffusion rate is not large. Then, a ratio of a volume to a surface area of the sample cell tube becomes small and heat is liable to leak, and therefore measurement error is involved in a measured heat capacity. Moreover, an amount of heat leak differ slightly depending upon kinds of liquids and filling conditions of the sample cell tube, i.e. whether the tube is filled with a sample or not.

Due to the above explained problem, the measurement accuracy of the heat capacity of the sample is at most ±0.2% in the known light irradiation type AC calorimetry. However in recent technological trend, it has been required keep the measurement accuracy of the heat capacity of the liquid sample less than ±0.2%. It is apparent that such a requirement could not be satisfied.

Furthermore, in the known AC calorimetry, a sample is heated in a periodic manner by periodically cutting off a the light beam emitted from a halogen lamp with the aid of a chopper. However, light intensity of the light source is not strictly constant, and generally decreases with time, and thus the light irradiation heating is not suitable for the measurement in which irradiation time has to be prolonged in order to raise the measurement accuracy. In this manner, the measurement error is increased due to light intensity. Moreover, the known light irradiation type AC calorimetry has a defect in that a large size light source and a large size light chopper are needed, so that the light source equipment is liable to be complicated and large. Furthermore, it is necessary to provide an opening in the thermal bath in order to pass the irradiation light onto the sample cell tube. It is apparent that such an opening decreases the faculty of the thermal bath and gives a possibility of introducing another measurement error.

SUMMARY OF THE INVENTION

It is an object of this invention to provide a novel and useful method of measuring an absolute value of heat capacity of a sample with extremely high accuracy without being influenced by the heat leakage.

It is another object of this invention to provide an AC calorimetric method, in which the above defect of the known light irradiation type AC calorimetry can be avoided and heat capacity of a sample can be measured with a decreased measurement error by heating the sample uniformly.

According to a first aspect of the invention, a method of measuring heat capacity of a sample comprises the steps of:

applying an AC heat to a sample whose heat capacity is to be measured with a given repetition frequency from an AC heat source;

detecting an AC temperature of the sample; and measuring the heat capacity of the sample from an amplitude of the AC temperature and a phase difference between the AC heat and the AC temperature.

According to this method of the present invention, the heat capacity is derived from the phase difference between the AC heat and the AC temperature and the amplitude of the AC temperature. Therefore, the influence of heat leakage can be eliminated and thus the heat capacity can be measured extremely precisely.

According to a second aspect of the invention, a method of measuring heat capacity of a liquid sample by using a sample cell having a tube which can contain the liquid sample, provided within an inner space of a thermal bath, comprises the non-sequential steps of;

(a) applying an AC heat to the sample cell by supplying an AC current having a given frequency directly to the tube of the sample cell, while the tube is kept vacant, and detecting a first amplitude of AC temperature of the tube and a first phase difference between the AC heat and the AC temperature;

(b) applying the AC heat to the sample cell by supplying the AC current to the tube of the sample cell, while the tube is filled with a standard liquid sample having known heat capacity, and detecting a second amplitude of AC temperature of the tube and standard liquid sample and a second phase difference between the AC heat and the AC temperature; and (c) applying the AC heat to the sample cell by supplying the AC current to the tube of the sample cell, while the tube is filled with a liquid sample whose heat capacity is to be measured, and detecting a third amplitude of AC temperature of the tube and liquid sample and a third phase difference between the AC heat and the AC temperature;

wherein the heat capacity of the liquid sample is derived from said first, second and third amplitudes of the AC temperatures and said first, second and third phase differences between the AC heats and the AC temperatures.

In this method according to the second aspect of the invention, the heat capacity of the liquid sample is measured from the phase difference of the AC heat and the AC temperature as well as the AC amplitude so that the heat leakage of the known AC calorimetry can be abolished. Furthermore, the AC heat is applied by directly supplying the AC current, the above mentioned instability of the AC heat in the known light irradiation type AC calorimetry can be eliminated. Moreover, the phase of the AC heat can be precisely measured and the above heat leakage can be eliminated by directly heating the sample cell. Thus, the heat capacity of the liquid sample can be highly accurately measured.

In the method according to the invention, it is possible to use sample cells having various structures. For example, when a liquid sample and a standard liquid sample are electrically insulating, it is preferable to use a sample cell having a tube made of an electrically conductive material and having a thin wall. Then, the electrically insulating liquid sample in the sample cell tube can be heated by connecting both ends of the tube to an AC power supply. In case of using such a sample cell, the AC heat can be applied to the sample cell by directly supplying an AC current to the tube.

When at least one of the liquid sample and standard liquid sample is electrically conductive, the above mentioned tube made of the conductive material could not be used. In such a case, the AC heat can be applied by using a sample cell comprising a thin wall tube made of an electrically insulated material and a heater of conductive material applied on an outer surface of the tube, and by connecting the both ends of this heater to an AC power supply. As a matter of course, the electrically insulating liquid sample and standard liquid sample can be treated by using such a sample cell. Furthermore, other sample cells having different configurations may be used as will be explained later in detail.

The liquid sample to be measured and the standard liquid sample can be uniformly heated by using the above sample cells, so that the heat capacity can be highly precisely measured. By using the sample cell allowing the direct heating, the sample cell can be almost perfectly enclosed within the thermal bath, and therefore it is no more necessary to form an opening in the thermal bath for irradiating the tube like as the known light irradiation type AC calorimetry, and the component can be simplified and faculty of the thermal bath can be improved.

BRIEF DESCRIPTION OF THE DRAWINGS

FIG. 1 is a cross sectional view showing an embodiment of the sample cell for use in the heat capacity measuring method according to the invention;

FIGS. 2A and 2B are cross sectional views illustrating another embodiment of the sample cell according to the invention;

FIG. 4 is a block diagram showing a whole apparatus for carrying out the heat capacity measuring method according to the invention;

FIG. 5 is a graph showing the heat capacity data measured by the method according to the invention;

DESCRIPTION OF THE PREFERRED EMBODIMENTS

Figure 3A:
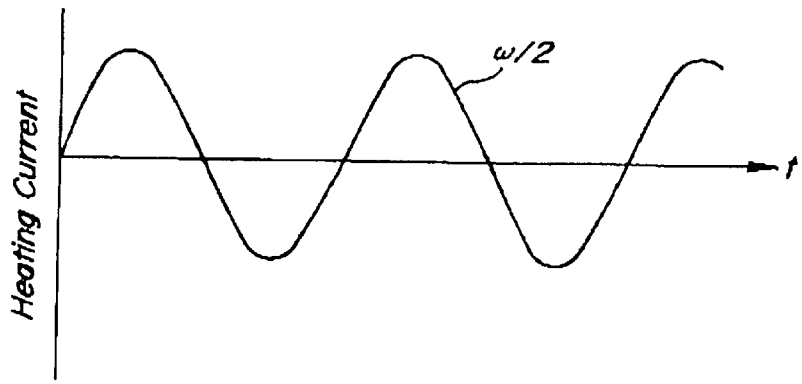
FIGS. 3A–3C are graphs representing the heating current, AC heat and AC temperature.

FIGS. 1 and 2 are cross sectional views showing two embodiments of the sample cell for use in the heat capacity measuring method according to the invention. The sample cell in FIG. 1 can be used when both a liquid sample whose heat capacity is to be measured and a standard liquid sample whose heat capacity is known are electrically insulating. The sample cell shown in FIG. 2 can be advantageously used when at least one of a liquid sample and a standard liquid sample is electrically conductive. However, this sample cell may be equally used for electrically insulating liquid sample and standard liquid sample.

Referring to FIG. 1, a sample cell 11 comprises a tube 12 made of an electrically conductive material such as stainless steel, copper and aluminum. The tube 12 may be filled with a liquid sample and standard liquid sample. A substantial part of the tube 12 is placed within a thermal bath 13. According to the invention, the sample cell 11 is directly heated in an alternate manner. In the present embodiment, a liquid sample contained in the tube 12 is heated by connecting both ends of the tube 12 of conductive material to an AC power supply. Then, an AC heating current flowed through the tube 12 to generate the AC heat. It is preferable that the material of the tube 12 does not react with the liquid sample, has high thermal conductivity for uniformly heating the liquid sample, has a suitable electrical conductivity for easily generating heat, and has small temperature dependence of electrical conductivity. It is also preferable that an inner diameter of the tube 12 is smaller than a heat diffusion length of a liquid sample, that a thickness of a wall of the tube is thin as far as possible, and that a length of the tube is longer than a heat diffusion length of a conductive material of the tube.

In this embodiment, the tube 12 is made of stainless steel, and has an inner diameter of about 290 $\mu$m, a wall thickness of about 20 $\mu$m, and a length of about 5 cm.

As shown in FIG. 1, the both ends of the tube 12 are extended out of a side wall of the thermal bath 13 and are connected, by means of flexible tubes 14 and 15, to a liquid-management system for selectively supplying liquid samples to be measured, standard liquid sample, washing liquids and so on to the tube 12. Since such a liquid-management system is well known in the art and does not constitutes a subject matter of the present invention, it is not shown in FIG. 1. A space 16 between the tube 12 and an inner wall of the thermal bath 13 is filled with air. Moreover, one ends of electrical lead wires 17 and 18 are connected to the both ends of the tube 12 projecting out of the thermal bath 13 and the other ends of these lead wires are connected to the AC power supply not shown.

To a substantially middle point of the tube 12, are adhered tips of first and second thermocouples 19 and 20 with an electrically insulating varnish. Heat capacity of these thermocouples 19 and 20 is preferably made as small as possible so as to obtain a sufficiently high response to the temperature amplitude to be detected.

In the embodiment illustrated in FIG. 2, similar components to those shown in FIG. 1 are denoted by the same reference numerals used in FIG. 1, and their detailed explanation is dispensed with. As depicted in FIG. 2B, a sample cell 21 of this embodiment, a tube 22 is made of an electrically insulating material, for example, glass. A heater 23 is provided on an outer surface of the tube 22 by vapor depositing a metal thereon. Both ends of the heater 23 are connected to the AC power supply by means of lead wires 17 and 18. In this embodiment, the heater 23 for heating a liquid sample contained in the tube is formed on a whole outer surface of the tube, and thus the liquid sample can be heated uniformly. Also in this embodiment, it is preferable to form the tube 22 to have a small inner diameter and a thin wall. In the present embodiment, the tube 22 is made of glass, and has an inner diameter of about 290 $\mu$m, a wall thickness of about 20 $\mu$m and a length of about 5 mm.

Now the method of measuring the heat capacity of a liquid sample using the sample cell 11 shown in FIG. 1 will be explained.

Firstly, the tube 12 of the sample cell 11 is kept vacant, and the lead wires 17 and 18 are connected to the AC power supply to apply an AC heat P·exp (i$\omega$t) to the tube, wherein $\omega$ is an angular frequency of an AC current supplied from the AC power supply. Then, an AC temperature of the tube 12 is measured by means of the first thermocouple 19 to derive an AC temperature detection signal representing an AC temperature $\Delta T_c$·exp i ($\omega$t−$\phi_c$). From the thus obtained AC temperature detection signal, are derived an amplitude $\Delta T_c$ of the AC temperature and a phase difference $\phi_c$ between the AC temperature and the AC heat. Now it is assumed that a thermal conductivity of the space 16 between the tube 12 and the thermal bath 13 is $K_c$ and a heat capacity in unit length of the tube 12 is $C_c$. Then, the AC temperature $\Delta T_c^*$ expressed in a complex number may be represented as follows:

$$\Delta T_c^* = \Delta T_c \cdot \exp(-i\phi_c) = P/(K_c + i \cdot C_c) \tag{1}$$

Next, an amplitude $\Delta T_r$ of an AC temperature $\Delta T_r$·exp i ($\omega$t−$\phi_r$) and a phase difference $\phi_r$ between the AC temperature and the AC heat are detected by applying the AC heat P·exp (i$\omega$t) to the tube 12 in the sample cell 11, while the tube 12 is filled with a standard liquid having known heat capacity $C_r$ and density $\rho_r$. Now it is assumed that a thermal conductivity of the space 16 between the tube 12 and thermal bath 13 is $K_r$, and a volume of unit length of tube 12 is V. Then, an AC temperature $\Delta T_r^*$ expressed in a complex number may be written as follows.

$$\Delta T_r^* = \Delta T_r \cdot \exp(-i\phi_r) = P/\{K_r + i\omega(C_c + V\rho_r C_r)\} \tag{2}$$

Finally, an amplitude $\Delta T_s$ of an AC temperature $\Delta T_s$·exp i ($\omega$t−$\phi_s$) and a phase difference $\phi_s$ between the AC temperature and the AC heat are detected by applying the AC heat P·exp (i$\omega$t) to the tube 12 in the sample cell 11 under such a condition that the tube 12 is filled with a liquid sample having heat capacity $C_s$ and density $\rho_s$. It is assumed that a thermal conductivity of the space 16 between the tube 12 and the thermal bath 13 enclosing the tube 12 is $K_s$. Then, an amplitude $\Delta T_s$ of the AC temperature is:

$$\Delta T_s^* = \Delta T_s \cdot \exp(-i\phi_s) = P/\{K_s + i\omega(C_c + V\rho_s C_s)\} \tag{3}$$

Now a manner of deriving the heat capacity of the liquid sample from the above equations (1)–(3) will be explained with reference to FIG. 3.

Figure 3B:
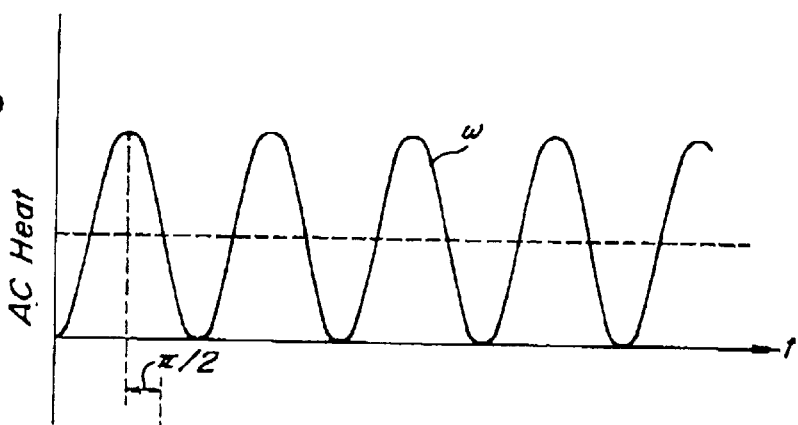
Figure 3C:
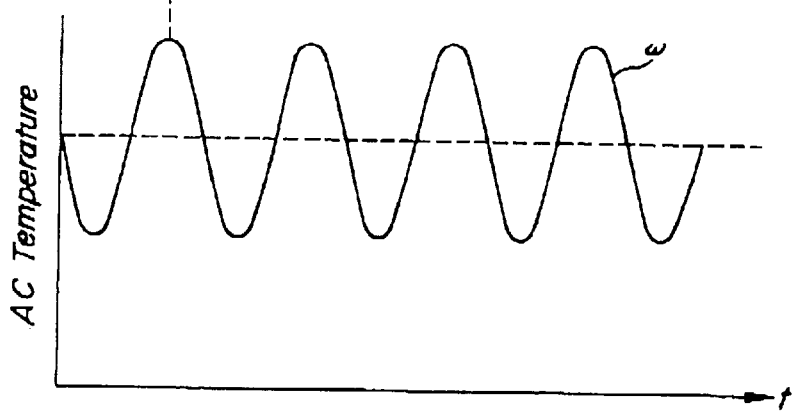

FIGS. 3A shows the heating AC current supplied to the heater, i.e. the conductive tube 12 of the sample cell 11, FIG. 3B represents the AC heat applied to the tube, and FIG. 3C shows the AC temperature of the tube.

First of all, from the above equation (1), the following equation (4) is obtained.

$$\Delta T_c^* = \Delta T_c \cdot \exp(-i\phi_c) = \Delta T_c \cdot \cos(\phi_c) - i\Delta T_c \cdot \sin(\phi_c) \tag{4}$$

Then, reciprocals of the both sides of the equation (4) may be expressed as follows:

$$\begin{aligned}
1/\Delta T_c^* &= 1/\{\Delta T_c \cdot \cos(\phi_c) - i\Delta T_c \cdot \sin(\phi_c)\} \\
&= 1/[\Delta T_c\{\cos(\phi_c) - i\sin(\phi_c)\}] \\
&= \{\cos(\phi_c) + i\sin(\phi_c)\}/\Delta T_c\{\cos^2(\phi_c) - i^2\sin^2(\phi_c)\} \\
&= \{\cos(\phi_c) + i\sin(\phi_c)\}/\Delta T_c \\
&= \cos(\phi_c)/\Delta T_c + i\sin(\phi_c)/\Delta T_c \\
&= (K_c + i\omega C_c)/P
\end{aligned} \tag{5}$$

Upon comparing real and imaginary parts of the equation (5) with each other, the following equations can be obtained:

$$K_c = P \cdot \cos(\phi)/\Delta T_c \tag{6}$$

$$C_c = P \cdot \sin(\phi_c)/(\omega \Delta T_c) \tag{7}$$

As can be seen from these equations, a component due to the thermal conductivity is distinguished from a component due to the heat capacity by in the term of phase. As shown in FIG. 3, $\phi_c$ can be described as $\phi_c \approx \pi/2$ when $K_c$ is sufficiently small.

Through similar calculations, the following equations may be derived From the equations (2) and (3).

$$K_r = P \cdot \cos(\phi_r)/\Delta T_r \tag{8}$$

$$C_c + V \cdot \rho_r \cdot C_r = P \cdot \sin(\phi_r)/\omega \Delta T_r \tag{9}$$

$$K_s = P \cdot \cos(\phi_s)/\Delta T_s \tag{10}$$

$$C_c + V \cdot \rho_s \cdot C_s = P \cdot \sin(\phi_s)/\omega \Delta T_s \tag{11}$$

Then, a heat capacity $\rho_s \cdot C_s$ per unit volume of the liquid sample to be measured may be expressed in the following manner:

$$\rho_s C_s = [\{(C_c + V\rho_s C_s) - C_c\}/\{(C_c + V\rho_r C_r) - C_c\}]\rho_r C_r \tag{12}$$

Putting the equations (7), (9), and (11) into the equation (12), the following equation (13) may be derived.

$$\rho_s \cdot C_s = [\{P\sin(\phi_s)/(\omega \Delta T_s) - P\sin(\phi_c)/(\omega \Delta T_c)\}/\{P\sin(\phi_r)/(\omega \Delta T_r) - P\sin(\phi_c)/(\omega \Delta T_c)\}]\rho_r \cdot C_r \tag{13}$$

Since $\omega$ and P may be assumed to be constant, the heat capacity $\rho_s \cdot C_s$ per unit volume of the liquid sample can be derived from the following equation (14).

$$\rho_s \cdot C_s = [\{\sin(\phi_s)/\Delta T_s - \sin(\phi_c)/\Delta T_c\}/\{\sin(\phi_r)/\Delta T_r - \sin(\phi_c)/\Delta T_c\}]\rho_r \cdot C_r \tag{14}$$

It should be noted that in the above calculations, $K_c$, $K_r$, and $K_s$ are not assumed to be equal to each other.

This is due to the fact that upon calculating the equations (7), (9) and (11), the contribution of the thermal conductivity K is deleted from the AC temperature amplitude $\Delta T$ by using the phase $\phi$ which is detected at respective measurements. Therefore, according to the invention, it is no more necessary to make $K_c$, $K_r$ and $K_s$ equal to each other. This is a crucial point of the heat capacity measuring method according to the invention. In this manner, according to the invention, the heat capacity of liquid sample can be measured accurately although the thermal conduction exists between the tube 12 and the thermal bath 13, and thus the problem of the known AC calorimetry that the measuring frequency has the lower limit can be advantageously removed.

FIG. 4 is a block diagram showing a whole construction of an embodiment of the measuring system for carrying out the heat capacity measuring method according to the invention. In this embodiment, the sample cell shown in FIG. 1 is used. The lead wires 17 and 18 having one ends connected to the both ends of the tube 12 made of metal are connected to a sine wave oscillator 31 serving as the AC power supply. The first thermocouple 19 is connected to a digital lock-in amplifier 33 through a transformer 32 serving as a matching impedance, and the second thermocouple 20 is connected to a digital voltmeter 34. Further, a temperature measuring Pt resistor 35 embedded in the thermal bath 13 is connected to a digital resistance-meter 36 in order to detect a temperature of the thermal bath 13.

The sine wave oscillator 31 is controlled by a computer 37, and an output signal of the oscillator is also supplied to the digital lock-in amplifier 33 as a standard phase signal. Moreover, outputs of the digital lock-in amplifier 33, the digital voltmeter 34, and the digital resistance 36 are supplied to the computer 37, in which the heat capacity of the liquid sample is calculated according to the above explained equations. As mentioned above, the both ends of the tube 12 in the sample cell 11 are coupled with the liquid-management system (not shown) through the flexible tubes 14 and 15, and liquid samples can be selectively supplied to the tube 12 in accordance with a predetermined measuring sequence. The operation of the sine wave oscillator 31 is controlled by the computer 37 in conjunction with the above mentioned measuring sequence. A temperature controller 39 for energizing a heater 38 is controlled by the computer 37 such that the thermal bath 13 is heated to a desired temperature.

Upon measuring the heat capacity, first of all, the heater 38 around the thermal bath is energized by the temperature controller 39 to heat the tube 12 of the sample cell 11 up to a desired temperature. During this step, a temperature difference between the thermal bath 13 and the outer surface of the tube 12 is measured with the aid of the second thermocouple 20, and the temperature of the thermal bath 13 is measured by means of the Pt resistance 35. Then, a temperature of the tube 12 can be measured as a sum of these temperatures. After it is confirmed that the temperature of the tube 12 has become stable at the desired temperature, the measurement is started.

First, the amplitude of the AC temperature $\Delta T_c$ of the tube 12 and the phase difference $\phi_c$ are measured by applying the AC heat to the tube 12 while the tube 12 of the sample cell 11 is kept vacant. Then, the amplitude of the AC temperature $\Delta T_r$ of the tube 12 and the phase difference $\phi_r$ are measured by applying the AC heat to the tube 12 having the standard liquid sample contained therein. Finally, the amplitude of the AC temperature $\Delta T_s$ and the phase difference $\phi_s$ are measured after introducing the liquid sample whose heat capacity is to be measured into the tube 12 in the sample cell 11. Also in this case, the AC heat is applied to the tube 12. In the computer 37, the thus measured amplitudes and phase differences are put into the equation (14) to derive the heat capacity $\rho_s \cdot C_s$ per unit volume of the liquid sample.

FIG. 5 shows a measurement result of a heat capacity within a temperature range (21–27° C.) near a gel-liquid crystal phase transition temperature of unilamellar vesicles of phospholipid dimyristoyl phosphatidylcholine. In this case, the measurement was conducted under such a condition that the standard liquid sample is pure water, the AC current frequency is 0.5 Hz, and the maximum AC amplitude is 80 mK.

It is obvious from FIG. 5 that the heat capacity of the liquid sample to be measured is measured within ±0.02% measurement accuracy, and its measurement accuracy is improved by more than 10 times as compared with the measurement accuracy (±0.2%) of the known AC calorimetry.

The present invention is not limited to the above explained embodiments, but many alternations and modifications are possible within the scope of the invention. For example, in the above embodiments, the temperature of the tube in the sample cell is measured by the thermocouple, but it may be measured by any other thermosensor having a sufficiently high precision. Further, the thermosensor may be arranged within the tube wall or may be inserted into the inner space of the tube through the tube wall. Furthermore, the temperature of the tube can be measured with a non contact type temperature measuring device.

In the embodiment, the space between the tube in the sample cell and the thermal bath is filled with air, but the space may be filled up with a gas having a known thermal conductivity, for example, nitrogen gas. Alternatively, the space may be drawn to a vacuum.

Figure 6:
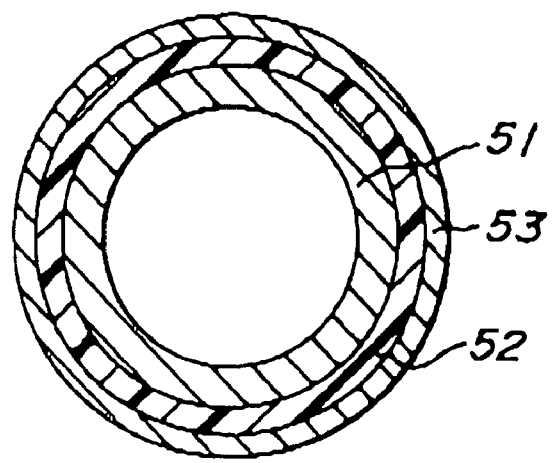
FIG. 6 is a cross sectional view showing another embodiment of the sample cell for use in the heat capacity measuring method according to the invention.

According to the invention, various types of the sample cells may be used. FIG. 6 is a cross sectional view showing another embodiment of the sample cell tube. In this embodiment, the tube comprises a main tube 51 made of an electrically conductive material, an electrically insulating film 52 applied on the outer surface of the main tube 51, and an electrically conductive layer 53 applied on the insulating film 52.

Figure 7:
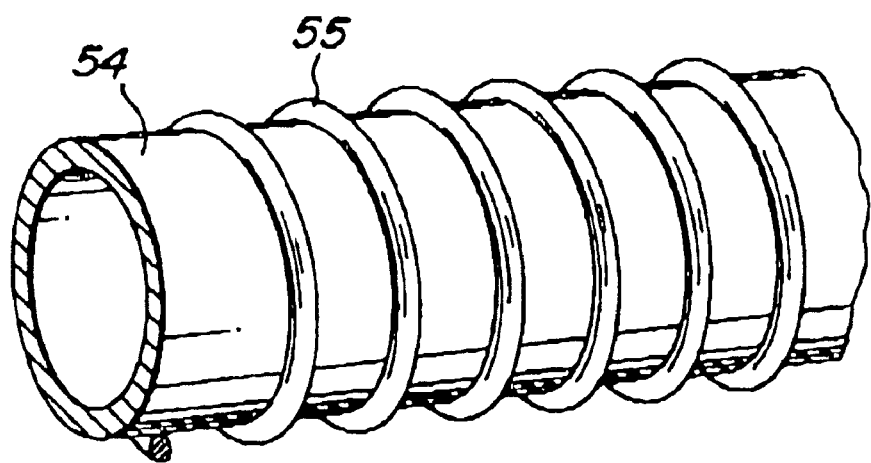
FIG. 7 is a perspective view depicting still another embodiment of the according to the invention.

In an embodiment of FIG. 7, the tube comprises a main tube 54 made of an electrically conductive material, and a heating wire 55 wound around the main tube 54 and including an core conductor and an insulating coating.

Furthermore, in the embodiment illustrated in FIG. 4, the output of the sine wave oscillator 31 is supplied to the digital lock-in amplifier 33 as the phase reference signal, but the output signal of the digital lock-in amplifier 33 may be supplied to the sine wave oscillator 31 to generate sine wave having a predetermined phase relationship with respect to that of the output signal from the digital lock-in amplifier 33.

In the above embodiment, the AC heat is applied to the sample cell by directly supplying the AC current to the tube. According to the invention, it is also possible to apply the AC heat to the tube by periodically irradiating the tube by means of the light chopper used in the known AC calorimetry. Even in this case, heat capacity of a sample can be measured much more precisely than the known AC calorimetry, because according to the invention, not only the amplitude of the AC temperature, but also the phase difference between the AC heat and the AC temperature are measured. Furthermore, in the above embodiments, heat capacity of liquid samples is measured, but according to the invention, heat capacity of gel, so1 and solid samples may be equally measured accurately.

In the method of measuring heat capacity of sample according to the invention, since the heat capacity of the sample is measured by detecting not only the amplitude of the AC temperature, but also the phase difference between the AC heat and the AC temperature, the heat capacity of sample can be measured highly precisely without being affected by heat leakage. Owing to the reason that the influence of the heat leakage is not necessarily considered, it is no more necessary to set the lower limit of the measurement frequency, and thus the measuring range can be widened.

Moreover, when the measurement is performed by introducing a liquid sample into the tube having a very thin wall, the liquid sample can be uniformly heated and the measurement accuracy can be much more improved. Furthermore, the structure of heating can be simpler. Thus, the heat capacity can be measured highly precisely, and in particular a change in heat capacity of a solution having a very small amount of substance or substances dissolved therein can be measured precisely with an extremely high measurement accuracy such as 0.02%.

What is claimed is:

1. A method of measuring heat capacity of a sample comprising the steps of:

applying an AC heat directly to a sample whose heat capacity is to be measured with a given repetition frequency from an AC heat source;

detecting an AC temperature of the sample; and measuring the heat capacity of the sample as a function of an amplitude of the AC temperature and a phase difference between the AC heat and the AC temperature.

2. A method according to claim 1, wherein said AC heat is applied to the sample by supplying an AC current to a heater provided in a vicinity of the sample.

3. A method according to claim 2, wherein said sample is introduced into a vessel including an electrically conductive material, and said heater is provided in said vessel.

4. A method according to claim 1, wherein said AC heat is applied to the sample by irradiating the sample with chopped light.

5. A method of measuring heat capacity of a liquid sample by using a sample cell having a tube which can contain a liquid sample, provided within an inner space of a thermal bath, comprising the non-sequential steps of:

(a) applying an AC heat directly to the sample cell by supplying an AC current having a given frequency directly to the tube of the sample cell, while the tube is kept vacant, and detecting a first amplitude of AC temperature of the tube and a first phase difference between the AC heat and the AC temperature;

(b) applying the AC heat to the sample cell by supplying the AC current to the tube of the sample cell, while the tube is filled with a standard liquid sample having known heat capacity, and detecting a second amplitude of AC temperature of the tube and standard liquid sample and a second phase difference between the AC heat and the AC temperature; and (c) applying the AC heat to the sample cell by supplying the AC current to the tube of the sample cell, while the tube is filled with a liquid sample whose heat capacity is to be measured, and detecting a third amplitude of AC temperature of the tube and liquid sample and a third phase difference between the AC heat and the AC temperature; wherein the heat capacity of the liquid sample is derived from said first, second and third amplitudes of the AC temperatures and said first, second and third phase differences between the AC heats and the AC temperatures.

6. A method according to claim 5, wherein said tube of the sample cell is made of an electrically conductive material, and both ends of the tube are connected to an AC current supply source to heat the sample cell tube and an electrically insulating liquid sample contained therein.

7. A method according to claim 5, wherein said tube of the sample cell is made of an electrically insulating material, a heater is applied on an outer surface of the tube, and the heater is connected to an AC current supply source to heat the sample cell tube and an electrically conductive or insulating liquid sample contained therein.

8. A method according to claim 5, wherein said tube of the sample cell is made of an electrically conductive material, an insulating film is applied on an outer surface of the tube, and a conductive film is applied on the insulating film to form a heater, and the heater is connected to an AC current supply source to heat the tube and an electrically conductive or insulating liquid sample contained therein.

9. A method according to claim 5, wherein said tube of the sample cell is made of an electrically conductive material, a conductive wire having an electrically insulating coating applied thereon is wound around the tube to form a heater, and said heater is connected to an AC current supply source to heat the tube and an electrically conductive or insulating liquid sample.

10. A method according to any one of claims 5–9, wherein when said first, second and third amplitudes of the AC heats are denoted by $\Delta T_c$, $\Delta T_r$ and $\Delta T_s$, respectively, said first, second and third phase differences are denoted by $\phi_c$, $\phi_r$ and $\phi_s$, respectively, and the heat capacity and a density of the reference liquid sample are denoted by $C_r$ and $\rho_r$, respectively, the heat capacity $\rho_s C_s$ per unit volume of the liquid sample is calculated by the equation $$\rho_s \cdot C_s = [[\{\sin(\phi_s)/\Delta T_s - \sin(\phi_c)/\Delta T_c\}/\{\sin(\phi_r)/\Delta T_r - \sin(\phi_c)/\Delta T_c\}] \rho_r \cdot C_r.$$

11. A method of measuring heat capacity of a sample comprising the steps of:
applying an AC heat directly to a sample cell from an AC heat source by conduction;
detecting an AC temperature of the sample; and
measuring the heat capacity of the sample as a function of an amplitude of the AC temperature and a phase difference between the AC heat and the AC temperature.

12. A method according to claim 11 wherein said heat source is in contact with the sample cell.

13. A method according to claim 11 wherein said AC heat source is connected to the sample cell.

14. A method of measuring heat capacity of a sample comprising the steps of:
applying an AC heat directly to a sample whose heat capacity is to be measured with a given repetition frequency from an AC heat source comprising a heater wire;
associating the sample cell functionally with said heater wire;
detecting an AC temperature of the sample; and
measuring the heat capacity of the sample as a function of an amplitude of the AC temperature and a phase difference between the AC heat and the AC temperature.

15. A method according to claim 14 wherein said heater wire is in contact with the sample cell.

16. A method according to claim 14 wherein said heater wire is wound around the sample cell.

* * * * *